US00PP07774P

United States Patent [19]

Yamamoto et al.

[11] Patent Number: Plant 7,774

[45] Date of Patent: Jan. 21, 1992

[54] DWARF GOLDEN MUGHO PINE NAMED 'YAMA GOLD AUREUS'

[76] Inventors: George Y. Yamamoto; Terry Y. Yamamoto, both of 5765 Sidney Rd. S.W., Port Orchard, Wash. 98336

[21] Appl. No.: 537,090

[22] Filed: Jun. 12, 1990

[51] Int. Cl.[5] ..... A01H 5/00

[52] U.S. Cl. ..... Plt./50

[58] Field of Search ..... Plt./50, 54, 50.1

[56] References Cited

PUBLICATIONS

Sunset Western Garden Book, 1988, Lane Publishing Co., Menlo Park, Calif., pp. 465, 469.

Harrison, 1975, "Ornamental Conifers", Hafner Press—Div. of MacMillan Pub. Co., New York, pp. 136–137.

*Primary Examiner*—Howard J. Locker

*Attorney, Agent, or Firm*—Christensen, O'Connor, Johnson & Kindness

[57] ABSTRACT

A new and distinct variety of dwarf Mugho pine characterized in that its needles are golden in color.

1 Drawing Sheet

BACKGROUND

This invention is a new and distinct variety of dwarf Mugho pine (*Pinus m. mugo*) that is characterized by its golden needles. It was discovered by applicants at their nursery, located at Port Orchard, Wash. The new Mugho pine, which is shown in FIG. 1 herein, was found growing naturally as a sport (an entire plant) in a cultivated area on the grounds of the nursery. The probable parentage is a normal dwarf Mugho pine. It has never been offered for sale. The applicants have named the new pine 'Yama gold aureus.'

'Yama gold aureus' was asexually reproduced by applicants at their nursery by grafting branches onto the root systems of other trees. The resulting grafted plants have been growing at applicants' nursery for nearly fifteen years and have maintained their golden needles as well as all other characteristic features throughout that time period. Examples of grafted plants are shown in FIG. 2 herein. Additionally, applicants have asexually reproduced the plant by propagating it from cuttings. The resulting plants have maintained the distinctive needle color as well as all other characteristic features of 'Yama gold aureus'. None of applicants' plants have produced any pine cones or seeds.

As noted above, 'Yama gold aureus' is characterized by the color of its needles, the majority of which have a brilliant golden color. Only a small number of needles that are obscured from sunlight remain green. The golden color of the needles does not change significantly during the year, although during the summer when new growth takes place, the newer needles tend to have a slightly more yellow color than the mature golden needles. The golden color is most brilliant in the winter season.

BRIEF DESCRIPTION OF THE DRAWINGS

Color photographs

TECHNICAL DESCRIPTION

Figure 1:
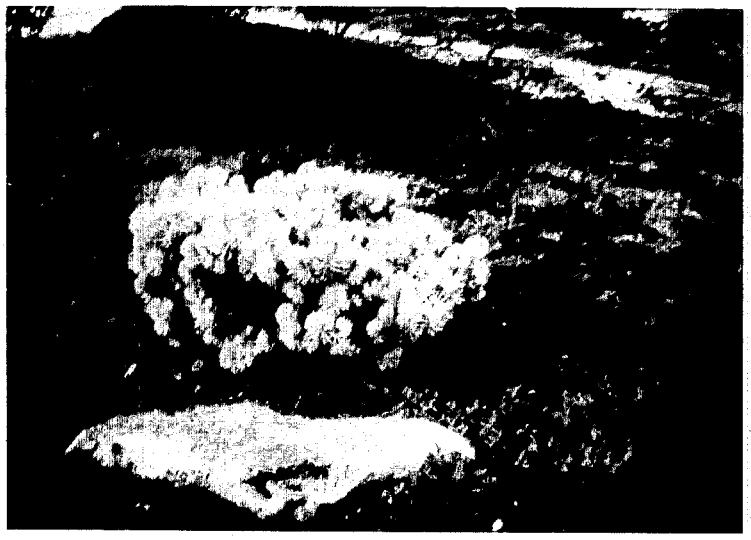
FIG. 1 shows the original sport growing at the nursery mentioned above.
Figure 2:
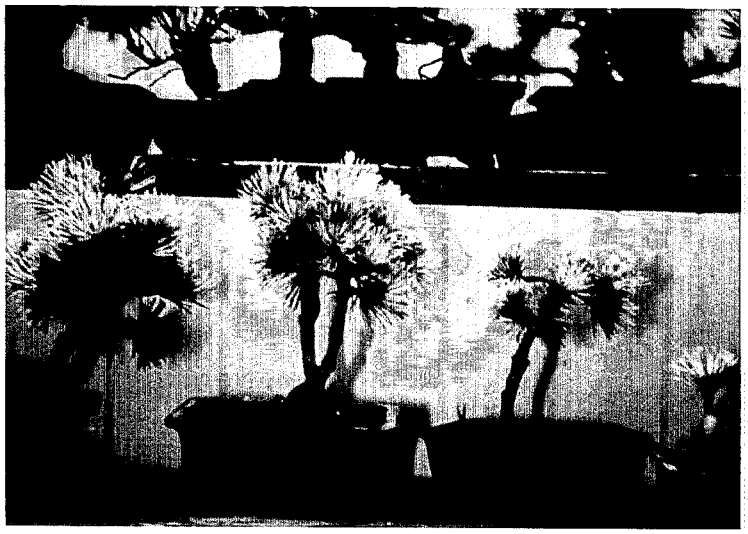
FIG. 2 shows typical examples of grafted plants that exhibit the golden needles of 'Yama gold aureus'. These grafted plants are approximately fifteen years old.

'Yama gold aureus' appears to have many of the same characteristics of a normal dwarf Mugho pine, *P. m. muga,* the notable exception being the color of the needles.

The needles of 'Yama gold aureus' have a color that ranges from 10L3 to 10L4 (tending more towards 10L3). (The color designations are based on those provided in *Dictionary of Color* by Maerz and Paul, McGraw-Hill Book Company, New York, 1930 Ed.). The above color designations correspond to the brightest golden coloration attained by the needles of 'Yama gold aureus'.

As with a normal dwarf Mugho pine, 'Yama gold aureus' produces its needles in bundles of 2. The needles are usually about 1 to 1½ inches in length.

The growth rate of 'Yama gold aureus' is quite slow. From infancy on, the pine tree is a shrubby dwarf pine with stout, crowded branches. At maturity, the tree or bush has a maximum height of about 18 inches to 24 inches.

The original sport that was discovered by applicants is still growing at their nursery after 25 years, and to date has not produced any observable flowers or cones. It is suspected that 'Yama gold aureus' does not have the capability to produce either flowers or cones.

Since 'Yama gold aureus' grows close to the ground, is fully branched and bears golden/yellow foliage year-round, it is a good ornamental for accent plantings and/or for difference in foliage, color and texture between plants. It can be high grafted, similar to the *Pine densifolia* 'Taniyoshi' which would create a specimen type plant. It can also be used for an attractive effect in a garden or planted in shallow pots and ornamentally shaped in the bonsai manner.

'Yama gold aureus' seems to have the same disease and frost resistance of *Pinus m. mugo.*

We claim:

1. A new and distinct variety of *Pinus m. mugo* (dwarf Mugho pine) substantially as herein shown and described, characterized particularly by its year-round golden needles.

* * * * *